United States Patent
Murphy (10) Patent No.: US 8,997,554 B2
(45) Date of Patent: Apr. 7, 2015

(54) METHOD AND APPARATUS FOR SOLID-LIQUID SEPARATION OF DRILLING FLUIDS FOR ANALYSIS

(75) Inventor: Robert J. Murphy, Kingwood, TX (US)

(73) Assignee: Halliburton Energy Services, Inc., Houston, TX (US)

(*) Notice: Subject to any disclaimer, the term of this patent is extended or adjusted under 35 U.S.C. 154(b) by 424 days.

(21) Appl. No.: 13/452,239

(22) Filed: Apr. 20, 2012

(65) Prior Publication Data

US 2013/0277113 A1  Oct. 24, 2013

(51) Int. Cl.
*E21B 21/06* (2006.01)
*G01N 1/40* (2006.01)
*G01N 33/28* (2006.01)

(52) U.S. Cl.
CPC ............ *G01N 1/4022* (2013.01); *E21B 21/065* (2013.01); *G01N 33/2823* (2013.01)

(58) Field of Classification Search
CPC ...... B01D 1/225; B01D 1/226; E21B 21/063; E21B 21/066–21/067; G01N 1/4022
USPC .................................................... 159/6.2, 6.3
See application file for complete search history.

(56) References Cited

U.S. PATENT DOCUMENTS

| | | | | |
|---|---|---|---|---|
| 2,065,619 A * | 12/1936 | Shinkle | .......................... | 208/185 |
| 3,260,655 A * | 7/1966 | Leo Mcgee Leonard et al. | .............. | 203/89 |
| 3,489,651 A * | 1/1970 | Pas Laddie A De | .......... | 202/187 |
| 3,521,691 A * | 7/1970 | Donovan James | ............. | 159/6.3 |
| 3,542,112 A * | 11/1970 | Monty | ........................... | 159/6.3 |
| 3,554,264 A * | 1/1971 | Baird et al. | ..................... | 159/6.3 |
| 3,554,266 A * | 1/1971 | Baird et al. | ...................... | 159/49 |
| 3,561,517 A * | 2/1971 | Donovan et al. | ............... | 159/6.3 |
| 3,644,179 A * | 2/1972 | Knoer et al. | ................... | 530/205 |
| 3,695,327 A | 10/1972 | Widmer | | |
| 3,891,495 A * | 6/1975 | Baird | ............................. | 159/6.3 |
| 4,649,655 A | 3/1987 | Witten | | |
| 4,872,954 A | 10/1989 | Hogan | | |
| 4,979,393 A | 12/1990 | Leung et al. | | |
| 5,028,297 A * | 7/1991 | Bracken | ......................... | 159/6.3 |
| 5,052,122 A * | 10/1991 | Ishikawa et al. | ................ | 34/302 |
| 5,078,836 A * | 1/1992 | Hogan | .............................. | 201/7 |
| 5,185,060 A * | 2/1993 | Yamasaki et al. | ............ | 159/13.1 |

(Continued)

FOREIGN PATENT DOCUMENTS

EP 0146531 A2 6/1985
JP 2002003859 A 1/2002

OTHER PUBLICATIONS

International Search Report and Written Opinion issued in related International Application No. PCT/US2013/037315, mailed Aug. 12, 2013, 11 pages.

*Primary Examiner* — John Fitzgerald
(74) *Attorney, Agent, or Firm* — Anthony Iannitelli; Baker Botts L.L.P.

(57) ABSTRACT

A system and method for solid-liquid separation and analysis of drilling fluids is described. The method includes heating a retort body to a pre-determined temperature, with an inner wall of the retort body at least partially defines a chamber within the retort body. A sample drilling fluid may be automatically injected into the inner chamber, and a film of the sample drilling fluid may be generated on the inner wall of the retort body. The film may be separated into a solid portion and a vapor. The method may further include collecting vapor using a vent that provides fluid communication with the inner chamber, and condensing the vapor into a fluid portion of the film. The volume of the fluid portion may them be automatically measured.

18 Claims, 5 Drawing Sheets

(56) References Cited

U.S. PATENT DOCUMENTS

| | | |
|---|---|---|
| 5,415,847 A * | 5/1995 | Robinson .................. 423/27 |
| 5,519,214 A | 5/1996 | Houwen et al. |
| 5,573,635 A * | 11/1996 | Van Der Piepen ............ 159/6.1 |
| 5,810,975 A * | 9/1998 | Bourdel .................... 202/176 |
| 8,142,634 B2 * | 3/2012 | McCosh ..................... 204/553 |
| 2010/0050466 A1 | 3/2010 | Titmas |

* cited by examiner

METHOD AND APPARATUS FOR SOLID-LIQUID SEPARATION OF DRILLING FLUIDS FOR ANALYSIS

BACKGROUND

The present disclosure relates generally to subterranean drilling operations and, more particularly, the present disclosure relates to a method and apparatus for solid-liquid separation of drilling fluids for analysis.

Subterranean drilling operations typically utilize drilling fluids to provide hydrostatic pressure to prevent formation fluids from entering into the well bore, to keep the drill bit cool and clean during drilling, to carry out drill cuttings, and to suspend the drill cuttings while drilling is paused and when the drilling assembly is brought in and out of the borehole. For an accurate measurement of oil to water ratio of a drilling fluid, or the solids in a drilling fluid, a mud retort is typically used. A mud retort may evaporate all of the liquid phases of the mud and condense the vapors so that the liquid volumes can be measured from a collector in which an oil phase migrates to the top and a water phase to the bottom.

Mud retorts typically require a series of manual steps to load the drilling fluid, measure the drilling distillate, and reset the retort to be used again. Typical mud retorts also include consumable pieces that must be replaced regularly. For example, the mud retort recommended by the America Petroleum Institute (API) in API RP 13B-2, "Recommended Practice for Field Testing of Oil-based Drilling Fluids," typically must be manually filled with a drilling fluid sample and a wad of steel wool must be placed at the top of the retort to prevent undistilled portions of the drilling fluid from escaping the retort. Once distilled, the fluid portions of the drilling fluid may be collected and manually measured. An operator must then manually reset the retort by cleaning out the solid portions of the drilling fluid left in the retort, which typically requires a cool-down time, and for the retort to be manually unscrewed to access the non-volatile drilling fluid solids. This process takes time and is not easily automated given the number of steps and the configuration of the API recommended retort. What is needed is an automated retort, which can operate autonomously on a drilling rig and can frequently make retort measurements and report them in near real time, which will allow more accurate control of the drilling mud properties for more efficient drilling.

FIGURES

Some specific exemplary embodiments of the disclosure may be understood by referring, in part, to the following description and the accompanying drawings.

While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

The present disclosure relates generally to subterranean drilling operations and, more particularly, the present disclosure relates to a method and apparatus for solid-liquid separation of drilling fluids for analysis.

Illustrative embodiments of the present disclosure are described in detail herein. In the interest of clarity, not all features of an actual implementation may be described in this specification. It will of course be appreciated that in the development of any such actual embodiment, numerous implementation-specific decisions must be made to achieve the specific implementation goals, which will vary from one implementation to another. Moreover, it will be appreciated that such a development effort might be complex and time-consuming, but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the disclosure. Embodiments of the present disclosure may be applicable to horizontal, vertical, deviated, or otherwise nonlinear wellbores in any type of subterranean formation. Embodiments may be applicable to injection wells as well as production wells, including hydrocarbon wells.

Figure 1:
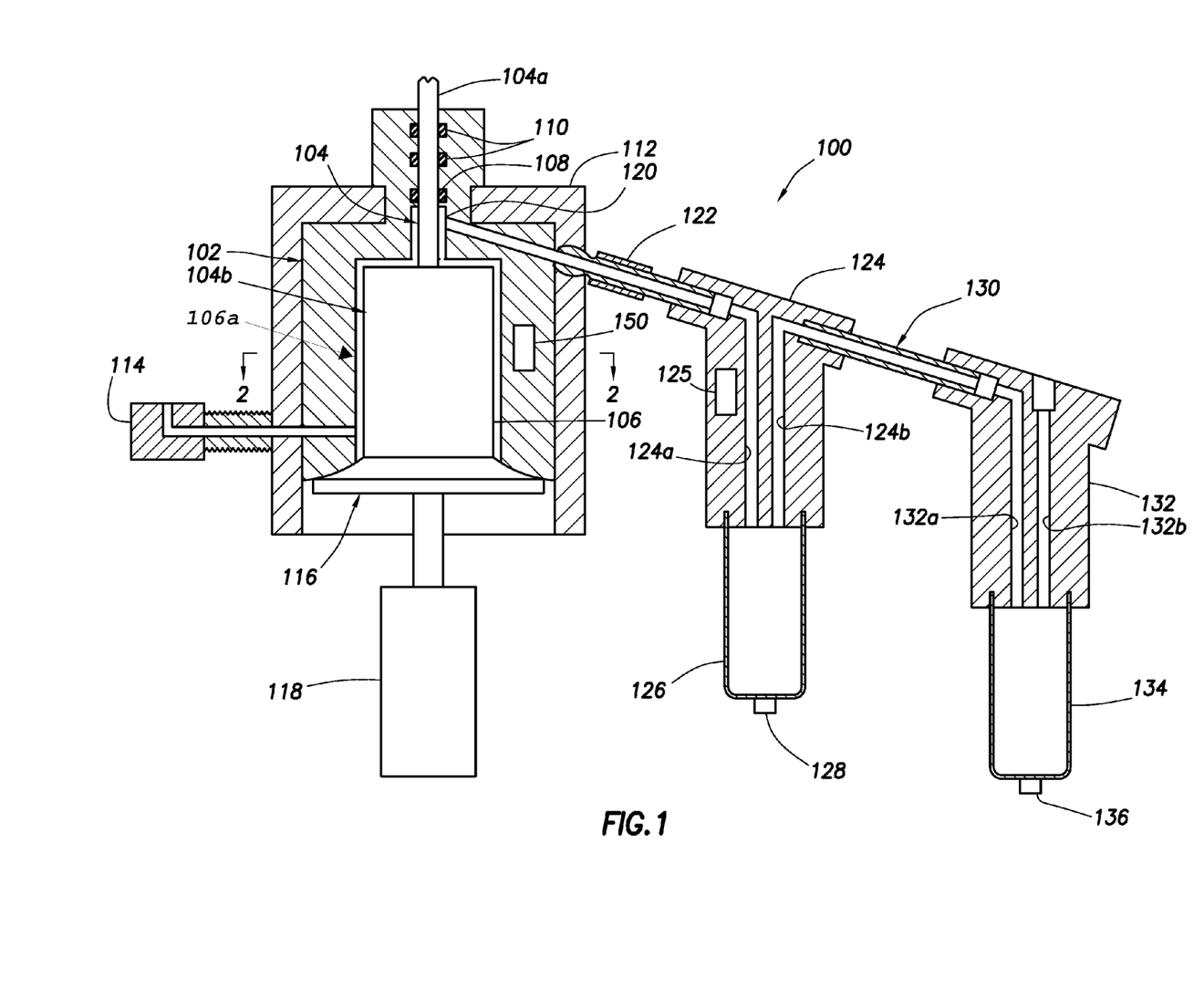
FIG. 1 illustrates a vertical cross section of an example apparatus, incorporating aspects of the present disclosure.

FIG. 1 illustrates an example apparatus 100 for solid-liquid separation and analysis of drilling fluids, according to aspects of the present disclosure. The apparatus includes a retort body 102. The retort body 102 may have a generally cylindrical outer surface, and may include an inner wall 106a that at least partially defines an inner chamber 106. The inner chamber 106 may be further defined by a plate 116 that is sealably and removably engaged with the retort body 102. As can be seen, the plate 116 may be coupled to an actuator 118 which, when extended, may force the plate 116 into a sealing engagement with the retort body 102, and when retracted, may provide access to the inner chamber 106, as will be discussed below with reference to FIG. 4.

The apparatus 100 may further include a heating element 150, coupled to the retort body 102. In the embodiment shown, the heating element 150 is disposed within a cavity in the retort body 102, but other configurations are possible. For example, the heating element 150 may comprise a sleeve surrounding portions of the retort body 102, such that sufficient amounts of heat can be imparted to the retort body 102.

Additionally, the apparatus 100 may include a rotor 104 at least partially disposed within the inner chamber. The rotor 104 may be driven by a motor (not shown) and may include a shaft portion 104a and a blade portion 104b. The blade portion 104b may at least partially contact the inner wall 106 of the retort body 102, or may include a width that is less than the width or diameter of the inner wall by a certain tolerance, as will be discussed below. The blade portion 104b may take on a variety of configurations as would be appreciated by one of ordinary skill in the art in view of this disclosure. For example, the blade portion may include a helical shape or rollers, as described below with reference to FIGS. 3a and 3b. Bearings 108 may allow the rotor 104 to spin freely within the inner chamber, and seal 110 may seal around the shaft 104a of the rotor 104. The apparatus may further include a fluid injector 114 that is in fluid communication with the inner chamber through the retort body 102 and thermal insulating jacket 112, and may inject sample drilling fluid into the inner chamber 106. The thermal insulating jacket 112 may surround at least a portion of the retort body 102, and may minimize the heating power requirements for the retort body 102.

In operation, the heating element 150 may heat the retort body 102 to a pre-determined temperature, such as 930° F.±70° F., as recommended by the API. The fluid injector 114 may then inject a precise volume of a sample drilling fluid into the inner chamber 106. The rotor 104 may spin within the inner chamber 106 of the retort body 102, generating a film of the sample drilling fluid on the inner wall 106 by distributing or spreading the sample drilling fluid against the inner wall 106 of the retort body 106. The thickness of the film may be determined, for example, by the width of the blade portion 104b relative to the width or diameter of the inner wall 106a. In certain embodiments, the rate at which the sample drilling fluid is injected into the inner chamber 106 may be configured to ensure that the film is effectively created on the inner wall 106. As would be appreciated by one of ordinary skill in the art, by spreading the sample drilling fluid in a thin film on the heated inner wall 106a the fluid portion of the film may evaporate rapidly, decreasing the splattering that may occur as part of the evaporative process, and eliminating the requirement for a consumable product, such as steel wool in a typical mud retort, to capture the splattered particles.

As the liquid portion of the film evaporates, it forms vapors that may rise to the top of the retort body 102. The seals 110 between the shaft 104a and the retort body 102 may prevent the vapors from escaping the retort body 102 around the shaft 104a. Rather, the vapors may escape through a vent 120 that provides fluid communication with the inner chamber 106 through the retort body 102 and the thermal insulating jacket 112. As can be seen, the vent 120 may be coupled via connectors 122 with a first condenser 124, such that the first condenser 124 is in fluid communication with the inner chamber 106 of the retort body 102. The vapors may travel to the first condenser 124 and down an internal passage 124a within the first condenser. The first condenser may be maintained at an elevated temperature by heating element 125. In certain embodiments, the vapor may be entirely condensed in the first collector 124, and collected in the first condenser in a first collector 126 coupled to the first condenser 124. The first collector 126 may comprise a clear material, such as glass or plastic, such that the volume of fluids collected is visible through the collector. The volume of the condensed liquid may be measured to determine, for example, the oil-to-water ratio of the sample drilling fluids. In certain embodiments, as will be discussed below, the measurement process may be automated by attaching a first automated measurement apparatus (not shown) to the first collector 126, which may read the fluid volume levels and transmit the measurements to a control system. The first automated measurement apparatus may comprise an optical measurement apparatus which can identify a fluid within the first collector 126.

In certain embodiments, part of the vapors from the sample drilling fluid may be condensed in a second condenser 132, in fluid communication with the first condenser 124. The second condenser 132 may be kept at a lower temperature than the first condenser 124. In certain embodiments, the second condenser 132 may be kept at near ambient temperature. In other embodiments, the second condenser 132 may be kept below ambient temperature using a cooler (not shown). The dual condenser configuration, with each at different temperatures, may be advantageous because each condenser may collect a different chemical component of the vapor. For example, the first condenser 124 may collect chemical components of the vapor that condense at higher temperatures, such as oil. Chemical components of the vapor that condense at lower temperatures, such as water, for example, may travel through the first condenser 124 in vapor form and out of the first condenser 124 through passageway 124b. The vapor may then travel to the second condenser 132 through connector 130, and through passageway 132a within the second condenser 132. The chemical components of the vapor that condense at lower temperatures may then be collected in the second collector 134 of the second condenser 132. Additional condensers may be used, as indicated by passageway 132b from the second condenser 132.

Like the first collector 126, the second collector 134 may comprise a clear material, such as glass or plastic, such that the volume of fluids collected is visible through the collector. Also like the first collector 126, as will be discussed below, a second automated measurement apparatus (not shown) may be connected to the second collector 134. The second automated measurement apparatus may comprise an optical measurement apparatus which may read the fluid volume levels and transmit the measurements to a control system. Notably, the dual condenser configuration is advantageous because it may allow for the volume of different fluid types to be read separately. For example, in a single condenser configuration, the oil from the sample drilling fluid may sit atop the water from the sample drilling fluid, such that measuring the volume of the water content and oil content requires finding the separating line between the oil and the water in a collector. In contrast, in a dual condenser configuration, the oil and water volumes may be contained separately, making the measurement process easier.

Figure 2:
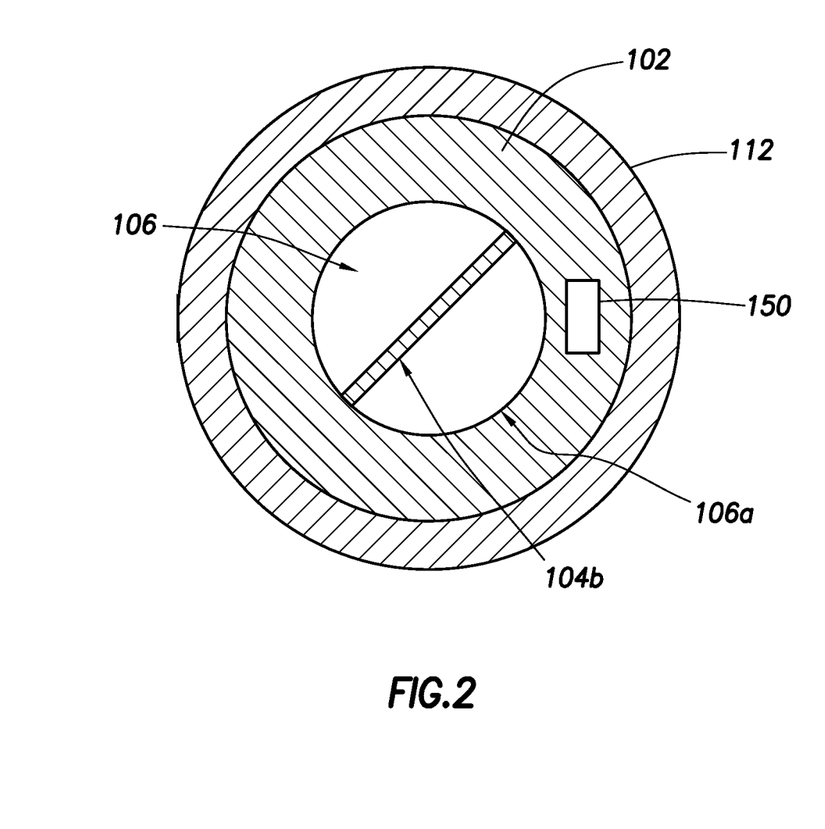
FIG. 2 illustrates a horizontal cross section of an example retort, according to aspects of the present disclosure.

FIG. 2 illustrates a cross section of the example retort shown in FIG. 1, along plane 2 in FIG. 1. As can be seen, the retort body 102 may comprise a solid annular structure with an inner wall 106a that at least partially defines an inner chamber 106. A thermal insulating jacket 112 may be disposed outside of and surround at least part of the retort body 102. The heating element 150 may be coupled to the retort body 102, or, in the embodiment show, be disposed within retort body 102.

As can be seen, blade 104b or rotor 104 may by disposed within the inner chamber 106 of the retort body 102. The blade 104b may comprise a planar, rigid body, as is shown in FIG. 2, or may take other shapes and configurations as will be described in FIGS. 3a and 3b. The blade 104b may be characterized by its dimension relative to the inner wall 106a of the retort body 102. In particular, the blade 104b may at least partially contact the inner wall 106 when it rotates within the retort body 102, or its width may be within a certain tolerance level of the diameter of the inner wall 106a, depending on the thickness of the film desired to be deposited on the wall. For example, the blade 104b may be sized such that it can spin freely within the retort body 102, while being close to the inner wall 106 such that the sample drilling fluid may be spread into a thin film along the inner wall 106. In certain embodiments, the blade 104b may scrape off the solid portion of the film left on the inner wall 106 after the fluid portion has been evaporated. This may prevent the build-up of solids on the inner wall 106 and help eject the solids from the retort body in preparation for the next sample drilling fluid, advantageously, without requiring the solids to be manually wiped from the inner wall 106a, or for the retort body 102 to be cooled so that the solids can be manually wiped.

Figure 3A:
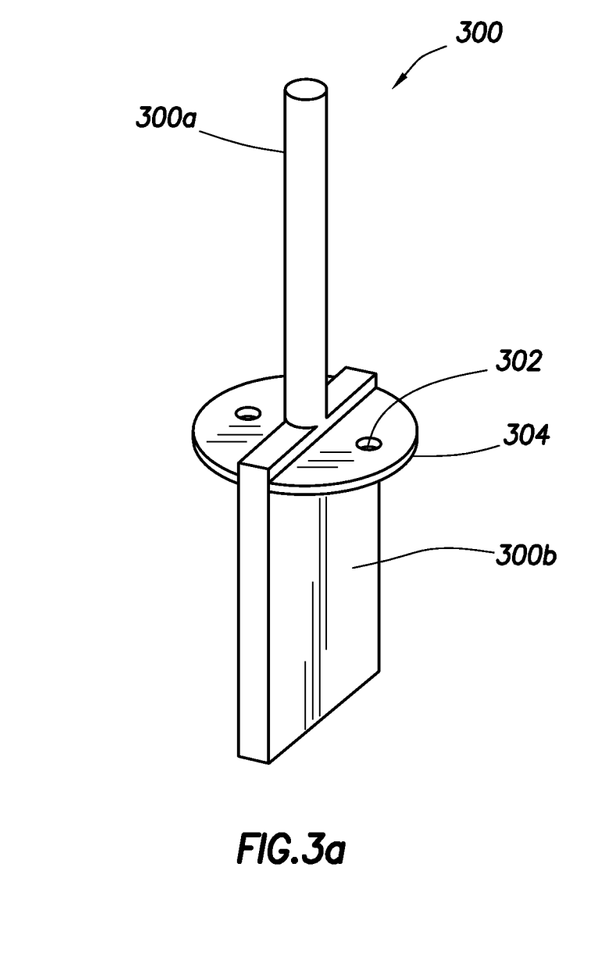
FIGS. 3a-b illustrate example rotors for use in a retort, according to aspects of the present disclosure.
Figure 3B:
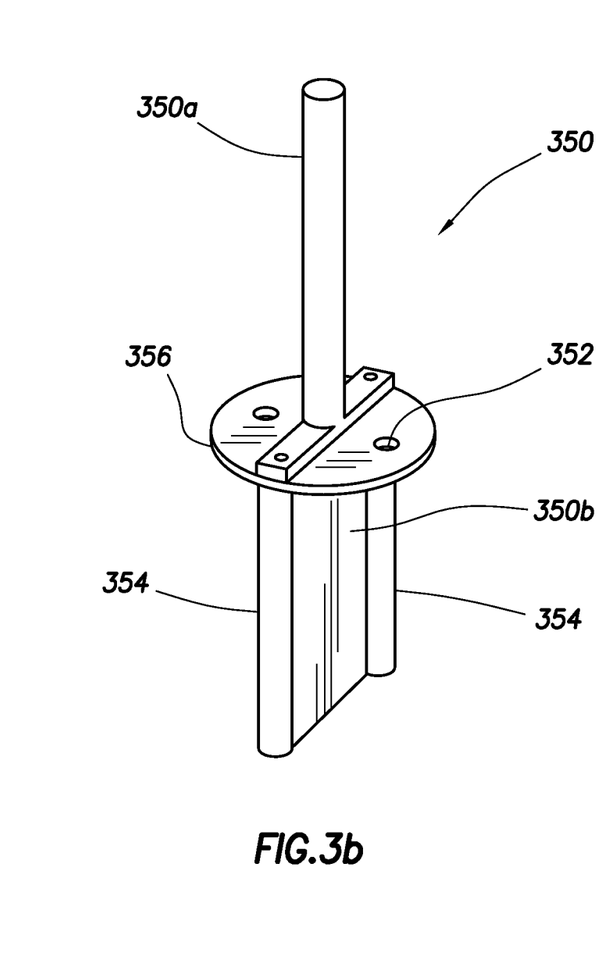

FIG. 3a illustrates an example rotor 300 which may be used in an apparatus comprising a retort body, similar to the apparatus shown in FIGS. 1 and 2. As can be seen, the rotor comprises a shaft 300*a* and a blade 300*b*. The blade 300*b* shown includes a rigid rectangular structure coupled to a disk 304 situated between the blade 300*b* and the shaft 300*a*. Holes 302 in the disk 304 provide a low resistance path for vapors to the venting area of the retort body 102. The blade 300*b* may be comprised, for example of metal or other rigid materials that would be appreciated by one of ordinary skill in view of this disclosure. The edges of the blade 300*b* may at least partially contact the inner wall of a rotor body in which it is installed. In an alternative embodiment, shown in FIG. 3*b*, the rotor 350 may include a shaft 350*a* and a blade 350*b*. In contrast to blade 300*b*, though, blade 350*b* may include rollers 354. As can be seen, the rollers may rotate one and be secured by pins through the disk 356 comprising vapor holes 352. When in use, the rollers 354 may rotate while contacting the inner wall of the rotor body in which the rotor 350 is installed, leaving a thin film of drilling fluid along the inner wall. The rotor configurations above are not meant to be limiting; other configurations are possible as would be appreciated by one of ordinary skill in the art in view of this disclosure.

Figure 4:
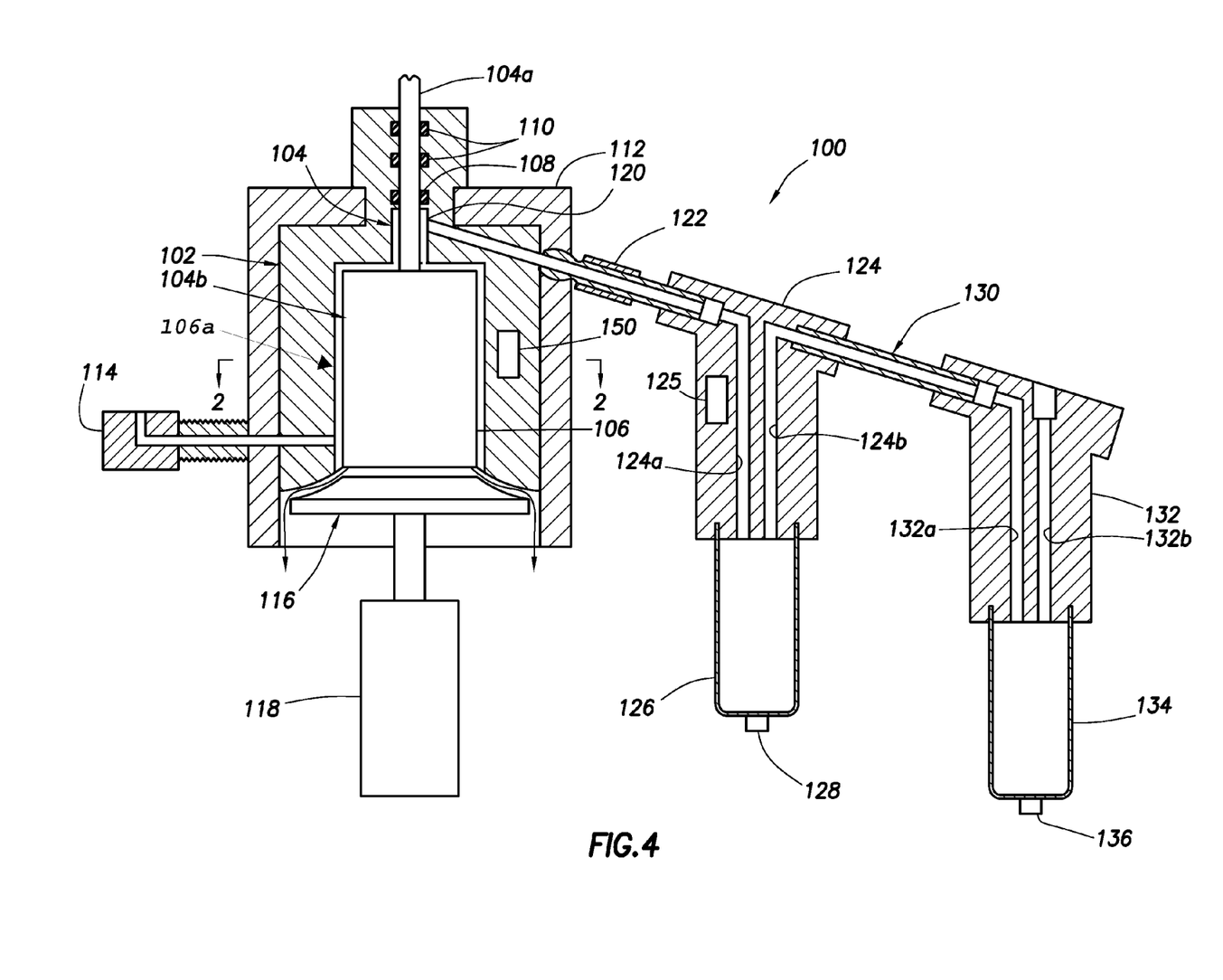
FIG. 4 illustrates a vertical cross section of an example apparatus, incorporating aspects of the present disclosure.

FIG. 4 illustrates the apparatus shown in FIG. 1, and in particular, how the apparatus shown in FIG. 1 may be automatically prepared for use. As can be seen, actuator 118 may retract, pulling the plate 116 away from its sealed engagement with retort body 102. By retracting the bottom plate, leftover solids within the retort body 102, after the evaporative process has been completed, may be scraped off of the inner wall 106*a*, and fall out of the bottom of the retort body 102. In some embodiments, a collector (not shown) may be coupled to the bottom of the apparatus to capture the solids for further measurement and disposal. After a pre-determined amount of time, the actuator 118 may extend, forcing the plate 116 into a sealed engagement with the retort body 102, allowing for the next sample drilling fluid to be injected. Notably, by using the actuator 118 and plate 116, the solids can be cleared automatically without an operator having to manually unscrew the retort to access the solids. Additionally, as will be discussed below, the actuator 118 may be coupled to an automated control system which may control the timing of the opening and closing of the plate 116.

In addition to plate 116, the apparatus may include other elements that may be used to automatically prepare the apparatus for the next sample drilling fluid. Collectors 126 and 134, for example, may include valves 128 and 136, respectively. When a sample drilling fluid is being processed, the valves 128 and 136 may be closed, trapping the condensed fluids within the collectors. After the measurement and analysis process is complete, however, the valves 128 and 138 may be opened, allowing for the fluids to be evacuated from the collectors. In certain embodiments, an auxiliary port (not shown) may be used to inject gas into the chamber 106 to sweep solids out of the chamber 106 when plate 116 is retracted. After plate 116 is closed, valves 128 and 136 may be opened and gas may be injected into the collectors 126 and 134, ejecting the fluids contained with collectors 126 and 134. In certain embodiments, the valves may be connected to tubes which may apply suction to the collectors, removing any excess fluids. In certain other embodiments, the valves 128 and 136 may be automated, as described below, such that an automated control system may trigger the valves 128 and 136 to open, for example, when the plate 116 is removed, as part of a process for preparing the apparatus for the next sample drilling fluid.

Figure 5:
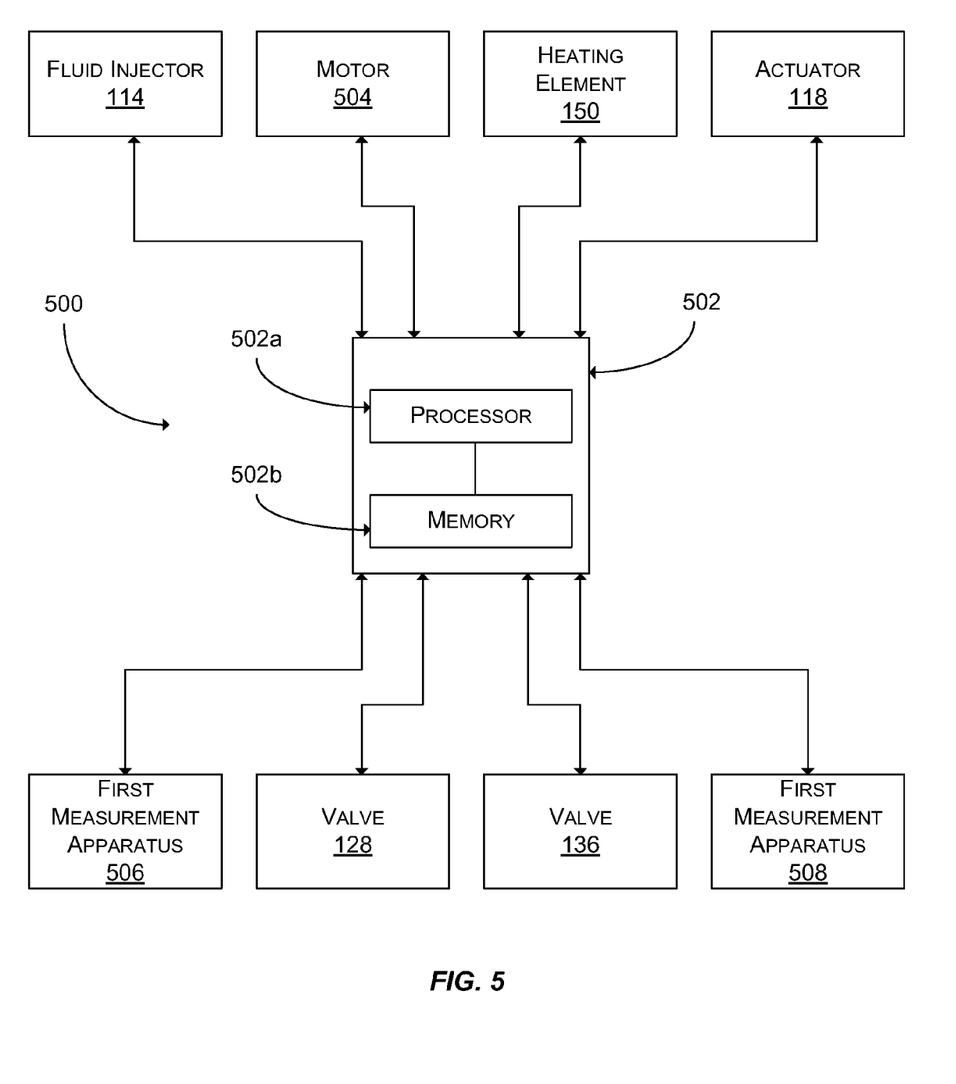
FIG. 5 illustrates an example apparatus including an automated control system, according to aspects of the present disclosure.

As would be appreciated by one of ordinary skill in view of this disclosure, the apparatus illustrated in the above figures may be advantageous because many of the steps needed to perform a mud retort analysis may be automated. For example, filling the retort with a sample, measuring the fluid levels, and cleaning the retort may all be performed automatically, whereas the structure of the API recommended retort makes automation difficult. In certain embodiments, some or all of the analysis described above may be controlled by an automated control system 500, as illustrated in FIG. 5. In certain embodiments, the automated control system 500 may comprise a Supervisory Control and Data Acquisition (SCADA) system. In certain embodiments, the SCADA system may be part of a larger system and report the measurements from the automated retort to the larger system. In certain embodiments, the measurements from the automated retort may be used to alter drilling mud properties.

As can be seen, the automated control system 500 may include a control unit 502, such as a computer system, that includes a processor 502*a* and memory coupled to the processor 502*b*. The control unit may be electrically or communicably coupled, via wires or other suitable transmission media, to elements of the analysis apparatus described above. For example, with respect to the retort body, such as retort body 102, the control unit 502 may be coupled to the fluid injector 114, the rotor motor 504, the heating element 150, and the actuator 118. The memory 502*b* may include instructions and parameters which cause the processor 502*a* to issue control signals to the elements, which may automatically control the process. For example, the control unit 502 may transmit to the fluid injector 114 control signals regarding the amount of drilling fluid to be injected into retort body, and the speed with which the drilling fluid should be injected. The control unit 502 may issue control signals to the rotor motor 504 controlling to rotational speed and the rotational direction of the rotor within the retort body. Likewise, the control unit 502 may issue control signals to the heating element 150 to manage the temperature of the retort, and the control unit 502 may control when the actuator 118 opens the retort to allow leftover solids to be ejected.

With respect to the condensers, such as first condenser 124 and second condenser 132, the control unit 502 may be communicably coupled to a first automated measurement apparatus 506 coupled to the first condenser 124 and a second automated measurement apparatus 508 coupled to the second condenser 132, and may trigger the apparatuses 506 and 508 to take measurements and may receive measurement signals from the apparatuses 506 and 508. In addition, the control unit 502 may control the temperature of the condensers by, for example, controlling heating element 125 in first condenser 124 or a cooler coupled to second condenser 132. Notably, the processor 502*a* of the control unit 500 may use the measurement values to analyze characteristic of the sample drilling fluid, including the oil/water ratio and the volume percent solids. Additionally, the control unit 502 may be coupled to valves 128 and 136, and may trigger the valves to open and close as part of the measurement or resetting process.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Also, the

What is claimed is:

1. A method, comprising:
maintaining a retort body at a pre-determined temperature, wherein an inner wall of the retort body at least partially defines a chamber within the retort body;
injecting a pre-determined volume of a sample drilling fluid into the inner chamber;
generating a film of the sample drilling fluid on the inner wall using a rotor comprising a rectangular blade portion with at least one roller that at least partially contacts the inner wall;
separating the film into a solid portion and a liquid portion, wherein separating the film into a liquid portion includes generating a vapor of the liquid portion; and
collecting the liquid portion using a vent that provides fluid communication with the inner chamber.

2. The method of claim 1, wherein the step of generating a film of the sample drilling fluid on the inner wall includes spinning a rotor within the chamber.

3. The method of claim 1, wherein the step of collecting the liquid portion includes condensing at least part of the vapor within a first condenser, wherein the first condenser is in fluid communication with the inner chamber.

4. The method of claim 3, wherein the step of collecting the liquid portion includes condensing at least part of the vapor portion within a second condenser, wherein the second condenser is in fluid communication with the first condenser, and wherein the second condenser is at a lower temperature than the first condenser.

5. The method of claim 4, further comprising the step of analyzing the sample drilling fluid, wherein analyzing the sample drilling fluid includes analyzing the contents of the first condenser and the second condenser.

6. The method of claim 5, wherein at least the steps of injecting the sample drilling fluid, generating a film of the sample drilling fluid, and analyzing the sample drilling fluid are automated using a Supervisory Control and Data Acquisition (SCADA) system.

7. The method of claim 6, further comprising the step of clearing the retort body, the first condenser, and the second condenser.

8. The method of claim 7, wherein the step of clearing the retort body, the first condenser, and the second condenser is automated using the SCADA system.

9. An apparatus for solid-liquid separation and analysis of drilling fluids, comprising:
a retort body, wherein the retort body comprises an inner wall that at least partially defines an inner chamber within the retort body;
a fluid injector in fluid communication with the inner chamber;
a rotor at least partially disposed within the inner chamber, wherein the rotor comprises a rectangular blade portion with at least one roller that at least partially contacts the inner wall;
a heating element coupled to the retort body; and
a first condenser in fluid communication with the inner chamber.

10. The apparatus of claim 9, wherein the fluid injector, rotor, and heating element are at least partially controlled by an automated control system, wherein the automated control system includes a processor and memory coupled to the processor, and wherein the memory includes control parameters related to the fluid injector, the rotor, and the heating element.

11. The apparatus of claim 10, further comprising an actuator coupled to a plate that defines a portion of the inner chamber, wherein the plate is removably and sealingly engaged with the retort body.

12. The apparatus of claim 9, further comprising a second condenser in fluid communication with the first condenser, wherein the second condenser is at a lower temperature than the first condenser.

13. The apparatus of claim 12, further comprising an first automated measurement apparatus coupled to the first condenser and a second automated measurement apparatus coupled to the second condenser.

14. The apparatus of claim 13, wherein the first automated measurement apparatus is coupled to a first collector of the first condenser, and the second automated measurement apparatus is coupled to a second collector of the second condenser.

15. An apparatus for solid-liquid separation and analysis of drilling fluids, comprising:
a retort, wherein the retort includes a retort body with an inner wall that at least partially defines an inner chamber within the retort body;
a fluid injector in fluid communication with the inner chamber, wherein the fluid injector is operable to inject a pre-determined volume of a sample drilling fluid into the inner chamber;
a rotor at least partially disposed within the inner chamber, wherein the rotor is driven by a motor, and wherein the rotor is operable to generate a film of the sample drilling fluid on the inner wall;
a first heating element coupled to the retort body, wherein the heating element is operable to heat the retort body to a first pre-determined temperature and to cause the film to separate into a solid portion and a vapor;
a first condenser in fluid communication with the inner chamber, wherein the first condenser is operable to condense at least part of the vapor into a first liquid portion and to collect the first fluid portion;
a second heating element coupled to the fluid condenser, wherein the second heating element is operable to heat the first condenser body to a second pre-determined temperature;
a first automated measurement apparatus coupled to the first condenser, wherein the first automated measurement apparatus is operable to measure the volume of the first liquid portion;
an automated control system, wherein the automated control system comprises a processor and a memory coupled to the processor, wherein the memory includes instructions that cause the processor to transmit control signals to at least the fluid injector, motor, and heating element, and to receive a measurement signal from the first optical measurement apparatus.

16. The apparatus of claim 15, wherein the automated control system comprises a Supervisory Control and Data Acquisition (SCADA) system.

17. The apparatus of claim 16, wherein the fluid injector, the rotor, the heating element, the first condenser and the first automated measurement apparatus are at least partially controlled by the SCADA system.

18. The apparatus of claim 17, wherein the first automated measurement apparatus comprises a first optical measurement apparatus coupled to a first collector of the first condenser.

* * * * *